United States Patent
Gruenanger et al.

(10) Patent No.: US 11,753,364 B2
(45) Date of Patent: Sep. 12, 2023

(54) METHOD FOR PRODUCING $C_2$-$C_4$ MONO ALKANOL AMINES USING AN ACID CATION EXCHANGER AS A CATALYST

(71) Applicant: BASF SE, Ludwigshafen am Rhein (DE)

(72) Inventors: Christian Gruenanger, Ludwigshafen am Rhein (DE); Gabriele Iffland, Ludwigshafen am Rhein (DE); Zeljko Kotanjac, Ludwigshafen am Rhein (DE); Hermann Luyken, Ludwigshafen am Rhein (DE); Thomas Krug, Ludwigshafen am Rhein (DE); Jian Zhong Yi, Ludwigshafen am Rhein (DE); Johann-Peter Melder, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 173 days.

(21) Appl. No.: 16/968,140

(22) PCT Filed: Jan. 28, 2019

(86) PCT No.: PCT/EP2019/051948
§ 371 (c)(1),
(2) Date: Aug. 6, 2020

(87) PCT Pub. No.: WO2019/154647
PCT Pub. Date: Aug. 15, 2019

(65) Prior Publication Data
US 2021/0363097 A1     Nov. 25, 2021

(30) Foreign Application Priority Data
Feb. 6, 2018 (EP) .................................... 18155331

(51) Int. Cl.
*C07C 213/04* (2006.01)
*B01J 8/06* (2006.01)
*B01J 31/08* (2006.01)

(52) U.S. Cl.
CPC ............. *C07C 213/04* (2013.01); *B01J 8/065* (2013.01); *B01J 31/08* (2013.01)

(58) Field of Classification Search
None
See application file for complete search history.

(56) References Cited

U.S. PATENT DOCUMENTS

| 3,697,598 | A | 10/1972 | Weibull et al. |
| 4,939,301 | A | 7/1990 | Grice et al. |
| 2003/0149305 | A1 | 8/2003 | Frauenkron et al. |
| 2017/0152216 | A1* | 6/2017 | Liao ............... C07C 253/18 |
| 2019/0039997 | A1 | 2/2019 | Ichikawa et al. |

FOREIGN PATENT DOCUMENTS

| CN | 1389297 A | 1/2003 |
| CN | 1436164 A | 8/2003 |
| CN | 103288657 A | 9/2013 |
| CN | 108367212 A | 8/2018 |
| CN | 108698979 A | 10/2018 |
| DE | 1941859 A1 | 3/1970 |
| GB | 1268237 A | 3/1972 |
| RU | 2225388 C1 | 3/2004 |
| SU | 682508 A1 | 8/1979 |
| SU | 791738 A1 | 12/1980 |
| WO | WO-2015034643 A1 | 3/2015 |
| WO | WO-2016144568 A1 | 9/2016 |
| WO | WO-2017095687 A1 | 6/2017 |
| WO | 2019/229156 A1 | 12/2019 |

OTHER PUBLICATIONS

International Search Report for PCT/EP2019/051948 dated Mar. 11, 2019.
Written Opinion of the International Searching Authority for PCT/EP2019/051948 dated Mar. 11, 2019.
"Ion Exchangers", Ullmann's Encyclopedia of Industrial Chemistry, ed. Elvers, et al., 5th Edition, vol. A14, Dec. 22, 1989, pp. 399-400.

* cited by examiner

*Primary Examiner* — Sudhakar Katakam
*Assistant Examiner* — Jennifer C Sawyer
(74) *Attorney, Agent, or Firm* — Faegre Drinker Biddle & Reath LLP

(57) ABSTRACT

A process for continuous production of $C_2$-$C_4$-monoalkanolamines by reaction of a corresponding $C_2$-$C_4$-alkylene oxide with a molar excess of ammonia ($NH_3$), wherein aqueous ammonia is employed, in the liquid phase and in the presence of an acidic cation exchanger as catalyst which contains a crosslinked copolymer comprising acidic functional groups as the carrier matrix, wherein the cation exchanger has a total exchange capacity of not less than 1.8 eq/L.

13 Claims, No Drawings

METHOD FOR PRODUCING $C_2$-$C_4$ MONO ALKANOL AMINES USING AN ACID CATION EXCHANGER AS A CATALYST

CROSS-REFERENCE TO RELATED APPLICATIONS

This application is a national stage application (under 35 U.S.C. § 371) of PCT/EP2019/051948, filed Jan. 28, 2019, which claims benefit of European Application No. 18155331.4, filed Feb. 6, 2018, both of which are incorporated herein by reference in their entirety.

The application relates to a process for continuous production of $C_2$-$C_4$-monoalkanolamines by reaction of a corresponding $C_2$-$C_4$-alkylene oxide with an excess of aqueous ammonia ($NH_3$) in the liquid phase and in the presence of a strongly acidic cation exchanger as catalyst which comprises a crosslinked copolymer comprising acidic functional groups as the carrier matrix.

PRIOR ART

Monoalkanolamines have a multiplicity of different possible uses. For example monoethanolamine (MEOA) is employed as an additive in cooling lubricants, as an additive in cleaning compositions and cosmetics or as an intermediate in the production of surfactants. Monoisopropanolamine (MIPOA) may be employed for example as a lubricant or as an intermediate in the production of surfactants.

Monoalkanolamines are produced on a large industrial scale by reaction of corresponding alkylene oxides with ammonia. The selectivity for the monoalkanolamine decreases with increasing conversion since the monoalkanolamine undergoes further reaction with the corresponding alkylene oxide to afford the dialkanolamine and the trialkanolamine.

The reaction of the alkylene oxide with ammonia proceeds catalytically. One possible catalyst is water. Higher selectivities for the monoalkanolamine are achievable for example through the use of zeolite catalysts or acidic cation exchangers.

DE 1941859 (Mo Och Domsjo Aktienbolag) discloses a process for producing monoalkanolamines, wherein acidic cation exchangers are employed. This process may further be performed in the presence of water.

WO 2015/034643 A1, WO 2016/144568 A1 and WO 2017/095687 A1 (all Dow Global Technologies LLC) describe the production of sulfonated cation exchangers based on styrene and divinylbenzene-containing copolymers.

In principle the use of aqueous ammonia may be advantageous. In the workup of the reaction mixture it is possible in the presence of water to remove ammonia from the reaction mixture at a lower pressure compared to a removal of ammonia without the presence of significant amounts of water. In existing plants in which water is employed as catalyst it may be possible to additionally employ an acidic cation exchanger to enhance the efficiency of the process. Naturally, the performance of such a cation exchanger must not be negatively affected by the presence of water.

The present invention accordingly had for its object to improve the economy of existing processes for producing monoalkanolamines and to remedy one or more disadvantages of the prior art. Thus, a process was to be found in which aqueous ammonia may be employed and which allows production of monoalkanolamines with high conversion and high yield, space-time yield [space-time yields are reported in 'amount of product/(catalyst volume·time)' (kg/($l_{cat}$·h)) and/or 'amount of product/(reactor volume·time)' (kg/($l_{reactor}$·h)], and selectivity. Such a process should, in particular, allow monoalkanolamines to be produced with high yields. As is well-known, yield is the product of conversion and selectivity. An improvement over the prior art may therefore consist in an increase in the conversion at unchanged selectivity or else in a higher selectivity at unchanged conversion. Naturally, a simultaneous increase of conversion and selectivity is particularly desirable.

Surprisingly found, to achieve the object specified above, was a process for continuous production of $C_2$-$C_4$-monoalkanolamines by reaction of a corresponding $C_2$-$C_4$-alkylene oxide with a molar excess of ammonia ($NH_3$), wherein aqueous ammonia is employed, in the liquid phase and in the presence of an acidic cation exchanger as catalyst which contains a crosslinked copolymer comprising acidic functional groups as the carrier matrix, wherein the cation exchanger has a total exchange capacity of not less than 1.8 eq/L.

DESCRIPTION OF THE INVENTION

According to the invention the term "alkylene oxide" is to be understood as meaning that the oxygen is located in the 1,2-position, i.e. that said molecule comprises an epoxy group. These include in particular ethylene oxide (EO), propylene oxide (PO), 1,2-butylene oxide, 2,3-butylene oxide and isobutylene oxide. The production of monoisopropanolamine (MIPOA) is preferably by reaction of propylene oxide (PO) and ammonia. The production of monoethanolamine (MEOA) is very particularly preferably by reaction of ethylene oxide (EO) and ammonia.

Description of the Cation Exchanger:

Employed as catalyst is an acidic cation exchanger which comprises a crosslinked copolymer comprising acidic functional groups as the carrier matrix. The terms carrier matrix or matrix may be used synonymously.

The acidic cation exchanger is typically employed in the $H^+$ form. That is to say the acidic functional groups are protonated and are not in the form of the sodium salt or the like. It is believed that on account of the ammonia present a deprotonation takes place in the course of the reaction and the acidic functional groups are then in the form of the corresponding ammonia salt.

The acidic functional groups have at least one acidic proton ($H^+$). Typically concerned are sulfonic acid ($—SO_3H$), carbonic acid ($—CO_2H$) or phosphorous acid groups ($—OPO(OH)_2$), preferably sulfonic acid groups.

The total absorption capacity of the cation exchanger according to the invention relates to the state thereof before contacting with the reactants ($C_2$-$C_4$-alkylene oxide and aqueous ammonia). It is preferably 1.8 to 3.0 eq/L, particularly preferably 1.8 to 2.5 eq/L and very particularly preferably 1.92 2.2 eq/L. The total exchange capacity in the unit eq/L represents the amount (in mol) of protons ($H^+$) bound in a liter of cation exchanger (in the $H^+$ form). Said capacity may be determined according to DIN 54403:2009-04. For strongly acidic cation exchangers such as (for example cation exchangers comprising sulfonic acid groups) method A of the abovementioned DIN standard is used and for weakly acidic cation exchangers (for example cation exchangers comprising carboxylic acid groups or phosphoric acid groups) method B of the abovementioned DIN standard is used. Cation exchangers such as for example Amberlite 252® H (1.7 eq/L, macroporous, moderately crosslinked) and Amberlite® 131 wet (1.35 eq/L, gel-like, sparingly crosslinked), both from Dow, are not catalysts/cation exchangers according to the invention on account of their low cation exchange capacity.

The cation exchangers according to the invention are preferably employed as spheres. The average diameters of such spheres may be 100 to 1000 μm. The diameter of the spheres may have a Gaussian distribution. Preference is given to a relatively uniform size distribution ("monodisperse"), wherein at least 90% by volume of the spheres have a diameter of 0.9 to 1.1 times the average diameter. It is preferable when the cation exchanger according to the invention is not milled.

The cation exchanger according to the invention may be either gel-like or macroporous. It is preferably macroporous. The terms gel-like and macroporous are familiar to those skilled in the art and describe the porosity of the cation exchanger. The term "macroporous" describes a cation exchanger having both macropores and mesopores. Mesopores have a diameter of about 20 Å to about 200 Å (Å=Angstrom; 1 Å=0.1 nm). Macropores have a diameter of more than about 200 Å. Gel-like cation exchangers have pores having a diameter of less than about 20 Å. Unlike a gel-like cation exchanger macroporous cation exchangers have a permanently porous structure, i.e. even in the dry, non-swollen state. By contrast, gel-like cation exchangers must first undergo swelling in order for their interior to be accessible for relevant reactants.

The macroporous cation exchangers preferably have a BET surface area of 10 to 100, in particular 15 to 40, m$^2$/g. The BET surface area may be determined by N$_2$ adsorption at the cation exchanger in the dry state.

The microporous cation exchangers preferably have an average pore diameter of 100 to 500 Å, particularly preferably 150 to 450 Å. The average pore diameter may be determined by N$_2$ adsorption at the cation exchanger in the dry state.

The crosslinked copolymer according to the invention is preferably moderately or highly crosslinked. Moderately crosslinked refers to copolymers having a degree of crosslinking of 8% to 15%. Highly crosslinked refers to copolymers having a degree of crosslinking of >15%. Sparingly crosslinked copolymers have a degree of crosslinking of <8%. The crosslinked copolymer according to the invention preferably has a degree of crosslinking of 8% to 25%, particularly preferably 11% to 24%, very particularly preferably 12% to 22%. The degree of crosslinking results from the ratio of the weight of the monomers which form at least one branching (for example a polyvinylidene monomer such as divinylbenzene, trivinylbenzene or ethylene glycol dimethylacrylate) to the total amount of all monomers multiplied by 100%. If for example production of a polymer employs a mixture of 11 g of divinylbenzene and 89 g of styrene the degree of crosslinking is as follows: 11 g/(11 g+89 g)*100%=11%.

A crosslinked copolymer according to the invention is preferably producible by polymerization of a mixture containing an aromatic C$_8$- to C$_{16}$-, preferably C$_8$- to C$_{14}$-monovinylidene monomer and an aromatic C$_{10}$- to C$_{20}$-, preferably C$_{10}$- to C$_{14}$-polyvinylidene monomer, particularly preferably C$_{10}$- to C$_{14}$-divinylidene monomer.

Such a mixture may comprise further aliphatic C$_3$- to C$_{14}$-monomers, comprising precisely one C=C-double bond and/or aliphatic C$_4$- to C$_{14}$-monomers comprising two or more double bonds.

A monovinylidene monomer has precisely one C=CH$_2$ group. A polyvinylidene monomer has at least two C=CH$_2$ groups and a divinylidene monomer has precisely 2 C=CH$_2$ groups. An aliphatic monomer in the context of the present invention comprises no aromatic ring system and may additionally comprise heteroatoms such as for example oxygen (O), chlorine (Cl) or bromine (Br). An aromatic monomer in the context of the present invention contains an aromatic ring system which conforms to the Hückel rule and may additionally comprise heteroatoms such as for example the abovementioned heteroatoms.

Examples of aromatic monovinylidene monomers are styrene and substituted styrene. Examples of substituted styrene are vinylnaphthaline, alpha-alkyl-substituted styrene (for example alpha-methylstyrene), alkylene-substituted styrene (for example vinyltoluene and ethylvinylbenzene) and also halogen-substituted styrene (for example bromo- or chloro-styrene and vinylbenzyl chloride). Very particular preference is given to styrene.

Examples of aromatic divinylidene monomers are divinylbenzene, divinyltoluene, divinylxylene, divinylnaphthalene or divinyldiphenylsulfone. Very particular preference is given to divinylbenzene.

One example of a polyvinylidene monomer is trivinylbenzene.

Examples of aliphatic monomers comprising a C=C double bond are acrylic acid, methacrylic acid, methyl methacrylate, isobornyl methacrylate, ethyl acrylate, ethylene, propylene, acrylonitrile, vinyl chlorides and mixtures of two or more of these monomers. One example of an aliphatic monomer comprising two C=C double bonds is butadiene or ethylene glycol dimethylacrylate.

The free-radical polymerization of the above-described mixtures of corresponding monomers and subsequent sulfonation, for example by means of concentrated sulfuric acid, oleum, chlorosulfonic acid or sulfur trioxide, is carried out under the customary conditions known to those skilled in the art. The production of macroporous cation exchangers is described in Ullmanns Encyclopedia of Industrial Chemistry, Vol. A14, 5$^{th}$ Ed., page 399, last paragraph, and page 400.

In a very particularly preferred embodiment the copolymer according to the invention is producible by polymerization of a mixture containing styrene and divinylbenzene. It is particularly preferable when said mixture consists of styrene and divinylbenzene. Once sulfonation has been carried out the molar ratio of sulfonic acid groups to phenyl radicals is preferably 1.1 to 2.0, particularly preferably 1.1 to 1.5, very particularly preferably 1.2 to 1.4.

Preferred commercially available cation exchangers are in particular Amberlyst® 35 wet (macroporous, highly crosslinked), Amberlyst® 36 wet (macroporous, highly crosslinked), Amberlyst® 40 wet (macroporous, highly crosslinked) from Dow, or Lewatit® K2620 from Lanxess.

Description of the Process:

The process according to the invention is carried out as a continuous operation.

The reaction of the C$_2$-C$_4$-alkylene oxide with ammonia is effected in the liquid phase. When operating in the liquid phase the reactants are simultaneously passed over the catalyst in the liquid phase, preferably at the pressure and temperature ranges recited below.

The catalyst is usually arranged in the reactor as a fixed bed. Preferred reactors are tubular reactors. Alternatively, the reaction may also be effected in a tube bundle reactor or in a single-stream plant. The catalyst is typically installed in the reactor in a damp state and subsequently washed with ammonia.

In a single-stream plant, the tubular reactor in which the reaction takes place may consist of a serially connected plurality (e.g., two or three) of individual tubular reactors. An intermediate introduction of feed (comprising the alkylene oxide and/or the ammonia) and/or reactor output from a downstream reactor is optionally advantageously possible here.

The catalyst space velocity is typically 0.5 to 5, preferably 0.8 to 2, kg of alkylene oxide per liter of catalyst per hour. The volume of the catalyst relates to the bulk volume of the moist cation exchanger (catalyst).

According to the invention aqueous ammonia is employed. This preferably has a water content of 0.1% to 30% by weight (based on $NH_3$). Particular preference is given to a water content of 0.1% to 20% by weight, 0.2% to 19% by weight, 0.5% to 18% by weight, 0.8% to 17% by weight, 0.9% to 16% by weight or 1% to 15% by weight, in each case based on $NH_3$. The term "based on $NH_3$" is to be understood as meaning that the amount of water is based exclusively on the amount of $NH_3$ without accounting for other components. For example in a mixture of 100 g of $NH_3$, 10 g of water and 2 g of other components the water content is 10% by weight.

Since the water that is present catalyzes the reaction it is useful to mix the ammonia and the alkylene oxide only immediately before contacting with the catalyst.

The reaction temperature is typically 30° C. to 150° C., preferably 40° C. to 140° C., particularly preferably 40° C. to 130° C. The reaction may be performed under isothermal or adiabatic conditions.

Under isothermal conditions the reaction temperature is preferably 50° C. to 140° C., particularly preferably 60° C. to 130° C. Since the reaction is strongly exothermic heat must be removed from the reaction mixture to keep the temperature approximately constant. This may be effected with cooling jackets for example.

The reaction may likewise be performed under adiabatic conditions. On account of the liberated heat of reaction the selected starting temperature rapidly increases. It is usually not necessary to remove heat from the reaction mixture. The maximum temperature in the reactor is preferably 70° C. to 140° C., particularly preferably 100° C. to 130° C.

The reaction pressure is to be chosen such that it is greater than the vapor pressure of the respective reaction mixture comprising alkylene oxide, ammonia and water at the respective reaction temperature. This ensures that the reactants are in the liquid phase. The reactor pressure is typically 80 to 150 bar, preferably 90 to 130 bar.

The ammonia is employed in molar excess. The molar ratio of ammonia to alkylene oxide is preferably 5 to 45. At ratios of less than 5 the yield of the monoalkanolamine is too low. At ratios of more than 45 a significant enhancement in yield is no longer registered. The use of a higher excess of ammonia and the accompanying additional complexity associated with the subsequent removal thereof from the reaction mixture are not economic. The ratio is particularly preferably 7 to 30, very particularly preferably 10 to 25. For the avoidance of doubt it is noted that the term "molar excess" and the abovementioned ratios are based on the ammonia without accounting for the water that is present according to the invention.

Once the reaction has taken place the obtained reaction mixture may be fractionated further. This is preferably carried out by distillation. This may comprise initially removing ammonia and water at a pressure in excess of standard pressure (1.013 bar) (for example in one or more suitable columns). The thus obtained aqueous ammonia is typically recycled into the reaction. The thus obtained mixture consists predominantly of the relevant monoalkanolamine but typically also contains small amounts of di- and trialkanolamines.

Depending on the application such a mixture may be employed directly or else may be subjected to further fractionation by distillation. This is typically effected using suitable columns. Said mixture is supplied to a first column and high-purity monoalkanolamine is removed overhead or via a sidestream takeoff. The resulting bottoms contain di- and trialkanolamines in predominant proportions. Said bottoms may be supplied to a second column in which high-purity dialkanolamine is removed overhead or via a sidestream takeoff. The bottoms product (it contains predominantly trialkanolamine) from the second columns may be supplied to a third column in which high-purity trialkanolamine is removed overhead or via a sidestream takeoff. Any high boilers accumulate in the bottom of the third columns.

The examples which follow serve to illustrate the invention, but without restricting it in any way.

Examples

Description of the Experiments:

Liquid ethylene oxide, liquid ammonia and water were independently pumped into a 2 ml stirred vessel (premixer) using HPLC pumps and therein mixed at a temperature of 33° C. and a pressure of 100-110 bar. The feed quantities and thus the quantity ratios were controlled via the HPLC pumps. The pressure of 100-110 bar ensured that a homogeneous liquid mixture was present. From the stirred vessel the reaction mixture arrived at 100-110 bar in a heated reactor tube having an external diameter of ⅛ inches, a wall thickness of 0.5 mm and a length of 1.35 m. The internal volume (about 5 ml) of this reactor tube was filled with the relevant cation exchanger and the reported space velocities relate to the bulk volume of the installed moist cation exchanger. The filled bulk volume was determined in a measuring cylinder during filling. Due to the small diameter of the reactor tube an approximately isothermal operating mode was ensured, thus ensuring comparability of the experiments. After passing through the reactor tube and a short cooling sector the reaction mixture was decompressed for sampling through a 6-port valve into aqueous acetic acid which brings the reaction to an immediate halt (protonation of the ammonia and ring opening of EO by acetic acid to afford glycol/glycol acetate). The reaction mixture acidified with acetic acid was derivatized with acetic anhydride for gas chromatographic (GC) analysis. The product distribution of MEOA, DEOA and TEOA (derivatized as acetate) was determined via a calibrated GC method. To this end, an "RXi-1-ms" GC column of 60 m in length was used with the following temperature program: Starting at 80° C., heating at 8° C./min to 280° C., 15 minutes at 280° C. The conversion was determined by means of the same calibrated method using the acetylated glycol amount (formed in the acetic acid treatment from unconverted EO and subsequent conversion with acetic anhydride).

The employed cation exchangers (all from Dow) have at least the following total exchange capacity.

| | | |
|---|---|---|
| Amberlite 252 ® H: | 1.7 eg/L | (noninventive) |
| Amberlite 131 ® wet: | 1.35 eq/L | (noninventive) |
| Amberlyst 35 ® wet: | 1.9 eq/L | (inventive) |
| Amberlyst 36 ® wet: | 1.95 eq/L | (inventive) |
| Amberlyst 40 ® wet: | 2.2 eq/L | (inventive) |

The following results show that the cation exchangers according to the invention provide an improved performance in respect of the yield at various molar ratios (ammonia to EO) and different water contents of the ammonia.

The results are shown in tables 1 to 4.

TABLE 1

| Cat. | T/° C. | Catalyst space velocity kg EO/ ($l_{cat}$ * h) | Molar ratio (NH$_3$/EO) | Water content based on NH$_3$/% by weight | Molar conversion based on EO/% | Product distribution/% by weight | | | Molar selectivity (MEOA)/ % | Molar yield (MEOA)/ % |
| --- | --- | --- | --- | --- | --- | --- | --- | --- | --- | --- |
| | | | | | | MEOA | DEOA | TEOA | | |
| Amberlite 252 H (noninventive) | 110 | 1.0 | 22 | 15 | 92.0 | 86.2 | 12.6 | 1.2 | 91.7 | 84.4 |
| Amberlite 131 wet (noninventive) | 110 | 1.0 | 20 | 15 | 95.9 | 80.9 | 16.8 | 2.3 | 88.3 | 84.7 |
| Amberlyst 36 wet (inventive) | 110 | 1.0 | 22 | 15 | 97.7 | 87.6 | 11.6 | 0.8 | 92.5 | 90.4 |
| Amberlyst 35 wet (inventive) | 110 | 1.0 | 20 | 15 | 95.3 | 87.9 | 11.3 | 0.8 | 92.7 | 88.4 |
| Amberlyst 40 wet (inventive) | 110 | 1.0 | 21 | 15 | 96.0 | 86.6 | 12.3 | 1.1 | 91.9 | 88.3 |

Compared to Amberlite 252 H the inventive catalysts provide a higher conversion without any accompanying reduction in selectivity. This is surprising to those skilled in the art. Those skilled in the art would actually have expected selectivity to decrease with an increase in conversion. Compared to Amberlite 131 wet, the inventive catalysts in fact provide a markedly higher selectivity at comparable conversion.

TABLE 2

| Cat. | T/° C. | Catalyst space velocity kg EO/ ($l_{cat}$ * h) | Molar ratio (NH$_3$/EO) | Water content based on NH$_3$/% by weight | Molar conversion based on EO/% | Product distribution/% by weight | | | Molar selectivity (MEOA)/ % | Molar yield (MEOA)/ % |
| --- | --- | --- | --- | --- | --- | --- | --- | --- | --- | --- |
| | | | | | | MEOA | DEOA | TEOA | | |
| Amberlite 252 H (noninventive) | 110 | 1.0 | 11 | 15 | 99.8 | 70.7 | 23.6 | 5.7 | 81.5 | 81.3 |
| Amberlite 131 wet (noninventive) | 110 | 1.0 | 10 | 15 | 99.8 | 63.9 | 26.7 | 9.3 | 76.8 | 76.6 |
| Amberlyst 36 wet (inventive) | 110 | 1.0 | 12 | 15 | 99.8 | 78.0 | 19.2 | 2.8 | 86.4 | 86.2 |
| Amberlyst 35 wet (inventive) | 110 | 1.0 | 11 | 15 | 99.9 | 78.5 | 19.2 | 2.3 | 86.6 | 86.6 |

Use of the cation exchanger according to the invention makes it possible to achieve a higher selectivity coupled with virtually complete conversion.

TABLE 3

| Cat. | T/° C. | Catalyst space velocity kg EO/ ($l_{cat}$ * h) | Molar ratio (NH$_3$/EO) | Water content based on NH$_3$/% by weight | Molar conversion based on EO/% | Product distribution/% by weight | | | Molar selectivity (MEOA)/ % | Molar yield (MEOA)/ % |
| --- | --- | --- | --- | --- | --- | --- | --- | --- | --- | --- |
| | | | | | | MEOA | DEOA | TEOA | | |
| Amberlite 252 H (noninventive) | 110 | 1.0 | 22 | 1 | 84.7 | 87.1 | 12.0 | 0.9 | 92.2 | 78.1 |
| Amberlite 131 wet (noninventive) | 110 | 1.0 | 23 | 1 | 72.0 | 86.2 | 12.3 | 1.5 | 91.7 | 66.1 |
| Amberlyst 36 wet (inventive) | 110 | 1.0 | 22 | 1 | 95.2 | 87.0 | 12.1 | 0.9 | 92.2 | 87.7 |
| Amberlyst 35 wet (inventive) | 110 | 1.0 | 20 | 15 | 90.7 | 89.4 | 10.1 | 0.5 | 93.6 | 84.9 |

The inventive catalysts provide a higher conversion without an accompanying reduction in selectivity. This is surprising to those skilled in the art. Those skilled in the art would actually have expected selectivity to decrease with an increase in conversion.

TABLE 4

| Cat. | T/° C. | Catalyst space velocity kg EO/ ($l_{cat}$ * h) | Molar ratio (NH$_3$/EO) | Water content based on NH$_3$/% by weight | Molar conversion based on EO/% | Product distribution/% by weight | | | Molar selectivity (MEOA)/ % | Molar yield (MEOA)/ % |
|---|---|---|---|---|---|---|---|---|---|---|
| | | | | | | MEOA | DEOA | TEOA | | |
| Amberlite 252 H (noninventive) | 110 | 1.0 | 11 | 1 | 97.6 | 75.0 | 21.6 | 3.4 | 84.3 | 82.3 |
| Amberlite 131 wet (noninventive) | 110 | 1.0 | 11 | 1 | 95.1 | 71.5 | 23.5 | 5.0 | 82.0 | 78.0 |
| Amberlyst 36 wet (inventive) | 110 | 1.0 | 12 | 1 | 99.7 | 77.4 | 19.7 | 2.9 | 86.0 | 85.7 |
| Amberlyst 35 wet (inventive) | 110 | 1.0 | 11 | 1 | 99.6 | 77.5 | 20.2 | 2.3 | 85.9 | 85.6 |

The inventive catalysts provide both a higher selectivity and a higher conversion.

The invention claimed is:

1. A process for continuous production of C2-C4-monoalkanolamines by reaction of a corresponding C2-C4-alkylene oxide with a molar excess of ammonia (NH3), wherein aqueous ammonia is employed, in the liquid phase and in the presence of an acidic cation exchanger as catalyst which contains a crosslinked copolymer comprising acidic functional groups as the carrier matrix, wherein the cation exchanger has a total exchange capacity of not less than 1.8 eq/L, is macroporous and the acidic functional groups are sulfonic acid groups.

2. The process according to claim 1, wherein the total exchange capacity is 1.8 to 2.5 eq/L.

3. The process according to claim 1, wherein the total exchange capacity is 1.9 to 2.2 eq/L.

4. The process according to claim 1, wherein the crosslinked copolymer is moderately crosslinked or highly crosslinked.

5. The process according to claim 1, wherein the crosslinked copolymer is producible by polymerization of a mixture comprising an aromatic C$_8$- to C$_{12}$-monovinylidene monomer and an aromatic C$_{10}$- to C$_{14}$-divinylidene monomer.

6. The process according to claim 5, characterized in that the crosslinked copolymer is producible by polymerization of a mixture consisting of styrene and divinylbenzene.

7. The process according to claim 1, wherein the aqueous ammonia has a water content of 0.1% to 20% by weight (based on NH$_3$).

8. The process according to claim 1, wherein the reaction temperature is 30° C. to 150° C.

9. The process according to claim 1, wherein the reaction pressure is 80 to 150 bar.

10. The process according to claim 1, wherein the molar ratio of ammonia to alkylene oxide is 5 to 45.

11. The process according to claim 1, wherein said process is performed as a continuous operation and the catalyst is arranged in the reactor as a fixed bed.

12. The process according to claim 11, wherein the catalyst space velocity is 0.5 to 5 kg of alkylene oxide per liter of catalyst per hour.

13. The process according to claim 1 for production of monoethanolamine (MEOA) by reaction of ethylene oxide (EO) and ammonia.

* * * * *